United States Patent
Saoji et al.

(10) Patent No.: US 8,751,006 B2
(45) Date of Patent: *Jun. 10, 2014

(54) CHANNEL-SPECIFIC ADJUSTMENT OF SOUND PROCESSING STRATEGIES BASED ON ELECTRODE IMPEDANCE

(71) Applicant: Advanced Bionics AG, Staefa (CH)

(72) Inventors: Aniket Saoji, Newhall, CA (US); Leonid M. Litvak, Los Angeles, CA (US)

(73) Assignee: Advanced Bionics AG, Zug (CH)

(*) Notice: Subject to any disclaimer, the term of this patent is extended or adjusted under 35 U.S.C. 154(b) by 0 days.

This patent is subject to a terminal disclaimer.

(21) Appl. No.: 13/919,544

(22) Filed: Jun. 17, 2013

(65) Prior Publication Data

US 2013/0282077 A1 Oct. 24, 2013

Related U.S. Application Data

(63) Continuation-in-part of application No. 13/571,679, filed on Aug. 10, 2012, now Pat. No. 8,527,058, which is a continuation of application No. 12/342,859, filed on Dec. 23, 2008, now Pat. No. 8,265,766.

(51) Int. Cl.
*A61N 1/372* (2006.01)
*A61N 1/36* (2006.01)
*H04R 25/00* (2006.01)

(52) U.S. Cl.
CPC .......... *A61N 1/36032* (2013.01); *A61N 1/36185* (2013.01); *A61N 1/37252* (2013.01); *H04R 25/505* (2013.01); *H04R 25/606* (2013.01); *H04R 2460/03* (2013.01)
USPC .................. 607/56; 607/32; 607/55; 607/57; 607/60

(58) Field of Classification Search
USPC ....................................................... 607/55–57
See application file for complete search history.

(56) References Cited

U.S. PATENT DOCUMENTS

| | | |
|---|---|---|
| 4,400,590 A | 8/1983 | Michelson |
| 4,532,930 A | 8/1985 | Crosby et al. |
| 4,592,359 A | 6/1986 | Galbraith |
| 4,947,844 A | 8/1990 | McDermott |

(Continued)

OTHER PUBLICATIONS

Non-Final Office Action received in U.S. Appl. No. 12/342,859, dated Dec. 12, 2011.

(Continued)

*Primary Examiner* — Carl H Layno
*Assistant Examiner* — Jon Eric C Morales
(74) *Attorney, Agent, or Firm* — ALG Intellectual Property, LLC

(57) ABSTRACT

An exemplary method includes a sound processing unit 1) directing an implantable cochlear stimulator to apply a plurality of stimulation pulses each having a first pulse width by way of a plurality of electrodes during a first stimulation frame, the plurality of electrodes including a first electrode and a set of remaining electrodes, 2) detecting a change in impedance of the first electrode, 3) adjusting, in response to the change in impedance of the first electrode, a pulse width parameter associated with the first electrode to define a second pulse width, and 4) directing the implantable cochlear stimulator to apply a stimulation pulse having the second pulse width by way of the first electrode and a plurality of stimulation pulses having the first pulse width by way of the set of remaining electrodes during a second stimulation frame subsequent to the first stimulation frame.

20 Claims, 10 Drawing Sheets

(56) References Cited

U.S. PATENT DOCUMENTS

| | | |
|---|---|---|
| 5,522,865 A | 6/1996 | Schulman et al. |
| 5,824,022 A | 10/1998 | Zilberman et al. |
| 6,219,580 B1 | 4/2001 | Faltys et al. |
| 6,272,382 B1 | 8/2001 | Faltys et al. |
| 6,308,101 B1 | 10/2001 | Faltys et al. |
| 7,107,101 B1 | 9/2006 | Faltys |
| 8,265,766 B1 * | 9/2012 | Kulkarni et al. ............ 607/56 |
| 2009/0125081 A1 | 5/2009 | Spitzer et al. |

OTHER PUBLICATIONS

Non-Final Office Action received in U.S. Appl. No. 13/571,679, dated Dec. 31, 2012.

* cited by examiner

CHANNEL-SPECIFIC ADJUSTMENT OF SOUND PROCESSING STRATEGIES BASED ON ELECTRODE IMPEDANCE

RELATED APPLICATIONS

The present application is a continuation-in-part application of U.S. patent application Ser. No. 13/571,679 (now U.S. Pat. No. 8,527,058), filed on Aug. 10, 2012, which application is a continuation application of U.S. patent application Ser. No. 12/342,859 (now U.S. Pat. No. 8,265,766), filed on Dec. 23, 2008. Both applications are incorporated herein by reference in their entireties.

BACKGROUND INFORMATION

The sense of hearing in human beings involves the use of hair cells in the cochlea that convert or transduce acoustic signals into auditory nerve impulses. Hearing loss, which may be due to many different causes, is generally of two types: conductive and sensorineural. Conductive hearing loss occurs when the normal mechanical pathways for sound to reach the hair cells in the cochlea are impeded. These sound pathways may be impeded, for example, by damage to the auditory ossicles. Conductive hearing loss may often be helped by the use of conventional hearing aids that amplify sound so that acoustic signals reach the cochlea and the hair cells. Some types of conductive hearing loss may also be treated by surgical procedures.

Sensorineural hearing loss, on the other hand, is due to the absence or the destruction of the hair cells in the cochlea which are needed to transduce acoustic signals into auditory nerve impulses. Thus, people who suffer from sensorineural hearing loss are unable to derive any benefit from conventional hearing aid systems.

To overcome sensorineural hearing loss, numerous cochlear implant systems—or cochlear prosthesis—have been developed. Cochlear implant systems generally employ an array of electrodes that is inserted into the cochlear duct. One or more electrodes of the array selectively stimulate different auditory nerves at different places in the cochlea based on the pitch of a received sound signal. Within the cochlea, there are two main cues that convey "pitch" (frequency) information to the patient. These are (1) the place or location of stimulation along the length of a cochlear duct and (2) the temporal structure of the stimulating waveform. In the cochlea, sound frequencies are mapped to a "place" in the cochlea, generally from low to high sound frequencies mapped from the apical to basilar direction. The electrode array is fitted to the patient to arrive at a mapping scheme such that electrodes near the base of the cochlea are stimulated with high frequency signals, while electrodes near the apex are stimulated with low frequency signals.

Each electrode implanted within a cochlea has a certain impedance associated therewith. These impedance values are often used to determine one or more stimulation parameters during an initial fitting session to fit a cochlear implant system to a patient. However, electrode impedances may change over time, thus resulting in decreased sound quality, distorted pitch, and/or system malfunction.

BRIEF DESCRIPTION OF THE DRAWINGS

The accompanying drawings illustrate various embodiments and are a part of the specification. The illustrated embodiments are merely examples and do not limit the scope of the disclosure. Throughout the drawings, identical or similar reference numbers designate identical or similar elements.

DETAILED DESCRIPTION

Channel-specific adjustment of sound processing strategies based on electrode impedance is described herein. As will be described in more detail below, a sound processing unit may 1) direct an implantable cochlear stimulator to apply a plurality of stimulation pulses (i.e., a plurality of stimulation current pulses) each having a first pulse width by way of a plurality of electrodes during a first stimulation frame, the plurality of electrodes including a first electrode and a set of remaining electrodes, 2) detect a change in impedance of the first electrode, 3) adjust, in response to the change in impedance of the first electrode, a pulse width parameter associated with the first electrode to define a second pulse width that compensates for the change in impedance of the first electrode, and 4) direct the implantable cochlear stimulator to apply a stimulation pulse having the second pulse width by way of the first electrode and a plurality of stimulation pulses having the first pulse width by way of the set of remaining electrodes during a second stimulation frame subsequent to the first stimulation frame.

By adjusting the pulse width for only those electrodes (i.e., channels) that have impedances that have changed (as opposed to adjusting the pulse width for all of the electrodes included in a multi-channel cochlear implant system), various benefits may be realized. For example, a consistent loudness level of an audio signal as perceived by the patient may be achieved by increasing, for example, the pulse width of stimulation pulses applied by way of electrodes whose impedances have increased for one reason or another. By increasing the pulse width for only those electrodes that have impedances that have changed, the stimulation rate may be minimally affected compared to scenarios in which the pulse width for all electrodes (regardless of whether their impedances have changed) is increased. Other benefits of the present methods and systems will be made apparent herein.

To facilitate an understanding of the methods and systems described herein, an exemplary cochlear implant system 100 will now be described in connection with FIG. 1. Exemplary cochlear implant systems suitable for use as described herein include, but are not limited to, those disclosed in U.S. Pat. Nos. 4,400,590; 4,532,930; 4,592,359; 4,947,844; 5,824,022; 6,219,580; 6,272,382; and 6,308,101. All of these listed patents are incorporated herein by reference in their respective entireties.

Figure 1:
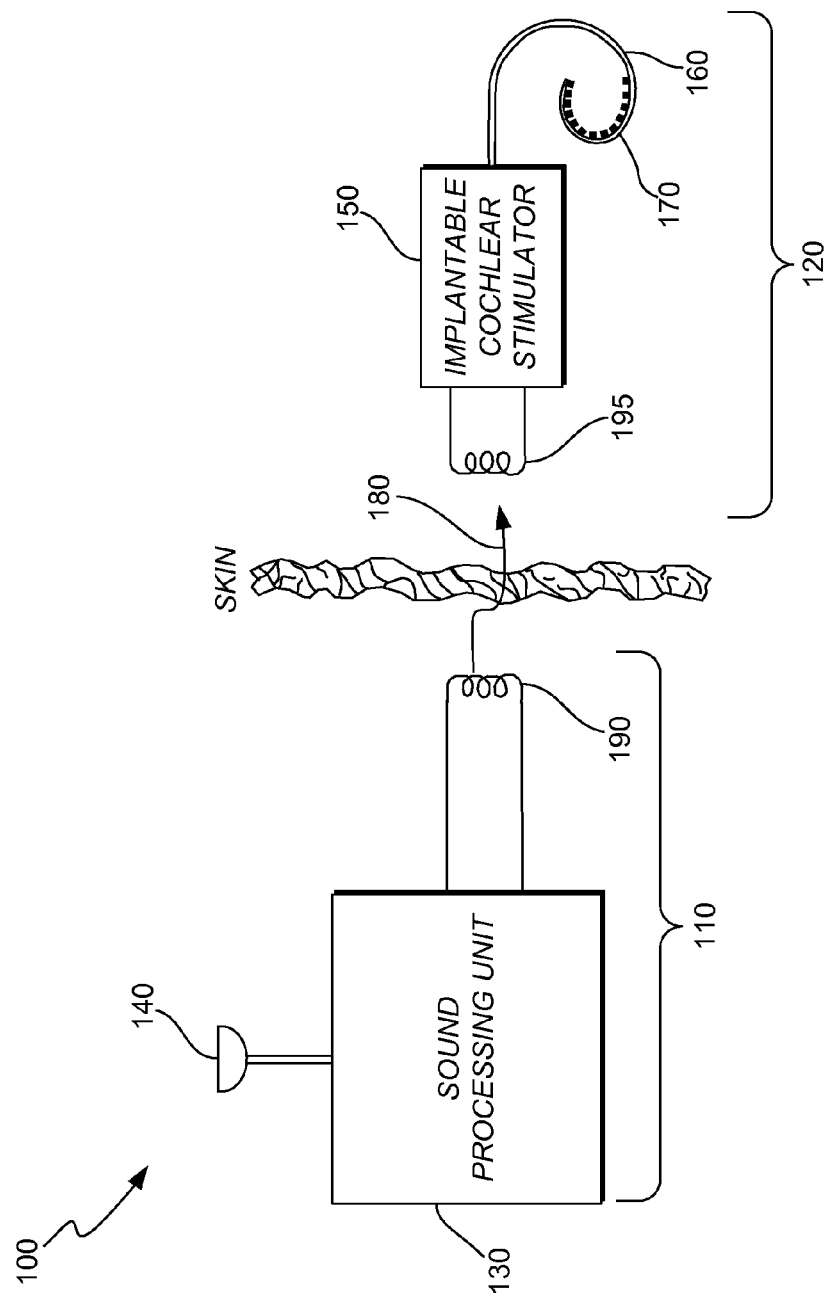
FIG. 1 illustrates an exemplary cochlear implant system according to principles described herein.

As shown in FIG. 1, the cochlear implant system 100, also referred to herein as a cochlear prosthesis, includes an external sound processor portion 110 and an implanted cochlear stimulation portion 120. The sound processor portion 110 may include a sound processing unit 130, a microphone 140, and/or additional circuitry as best serves a particular application. The cochlear stimulation portion 120 may include an implantable cochlear stimulator (ICS) 150, a lead 160 with an array of electrodes 170 disposed thereon, and/or additional circuitry as best serves a particular application. It will be recognized that the sound processor portion 110 may alternatively be located internal to the patient.

The microphone 140 of FIG. 1 is configured to sense acoustic signals and convert the sensed signals to corresponding electrical signals. The electrical signals are sent to the sound processing unit 130 over an electrical or other suitable link. Alternatively, the microphone 140 may be connected directly to, or integrated with, the sound processing unit 130.

The sound processing unit 130 may include any combination of hardware, software, and/or firmware as best serves a particular application. For example, the sound processing unit 130 may include one or more processors, digital signal processors (DSPs), filters, memory units, etc. In some examples, as will be described in more detail below, the sound processing unit 130 may include one or more alert facilities (not shown) configured to convey one or more alerts or other communications to a patient.

In some examples, the sound processing unit 130 may be configured to process the converted acoustic signals in accordance with a selected sound processing strategy to generate appropriate control signals or stimulation parameters for controlling the ICS 150. The electrical stimulation parameters may control various parameters of the stimulation current applied to a stimulation site including, but not limited to, frequency, pulse width, amplitude, waveform (e.g., square or sinusoidal), electrode polarity (i.e., anode-cathode assignment), location (i.e., which electrode pair or electrode group receives the stimulation current), burst pattern (e.g., burst on time and burst off time), duty cycle or burst repeat interval, ramp on time, and ramp off time of the stimulation current that is applied to the stimulation site.

It will be recognized that the sound processing unit 130 shown in FIG. 1 is merely illustrative of the many different sound processing units that may be used in connection with the present systems and methods. For example, the sound processing unit 130 may include a behind-the-ear (BTE) unit configured to be positioned behind the ear. Alternatively, the sound processing unit 130 may include a portable speech processor (PSP) device, a conventional hearing aid, or any other type of sound processing unit. In certain examples, the sound processing unit 130 may be removed from behind the ear or other operating location by the patient prior to sleeping and replaced upon waking.

The lead 160 of FIG. 1 is adapted to be inserted within a duct of a patient's cochlea. As shown in FIG. 1, the lead 160 includes an array of electrodes 170 disposed along its length. It will be recognized that any number of electrodes 170 may be disposed along the lead 160 as may serve a particular application.

Each of the electrodes 170 is electrically coupled to the implantable cochlear stimulator 150. Electronic circuitry within the implantable cochlear stimulator 150 may therefore be configured to apply stimulation current to selected pairs or groups of electrodes 170 in accordance with a specified stimulation pattern controlled by the sound processing unit 130.

As mentioned, the implantable cochlear stimulator 150 and lead 160 may be implanted within the patient while the sound processing unit 130 and the microphone 140 are configured to be located outside the patient, e.g., behind the ear. Hence, the implantable cochlear stimulator 150 and the sound processing unit 130 may be transcutaneously coupled via a suitable data or communications link 180. The communications link 180 allows power and control signals to be sent from the sound processing unit 130 to the implantable cochlear stimulator 150. In some embodiments, data and status signals may also be sent from the implantable cochlear stimulator 150 to the sound processing unit 130.

The external and implantable portions of the cochlear implant system 100 may each include one or more coils configured to transmit and receive power and/or control signals via the data link 180. For example, the external portion 110 of the cochlear implant system 100 may include an external coil 190 and the implantable portion of the cochlear implant system 120 may include an implantable coil 195. The external coil 190 and the implantable coil 195 may be inductively coupled to each other, thereby allowing data and power signals to be wirelessly transmitted between the external portion and the implantable portion of the cochlear implant system 100. Because in certain embodiments, the external portion 110 of the cochlear implant system 100 may not always be within close proximity to the implantable portion of the cochlear implant system 120, such as when the external portion 110 is removed for sleeping, the system may be configured to recognize when the implantable coil 195 and the external coil 190 are within range of one another.

Figure 2:
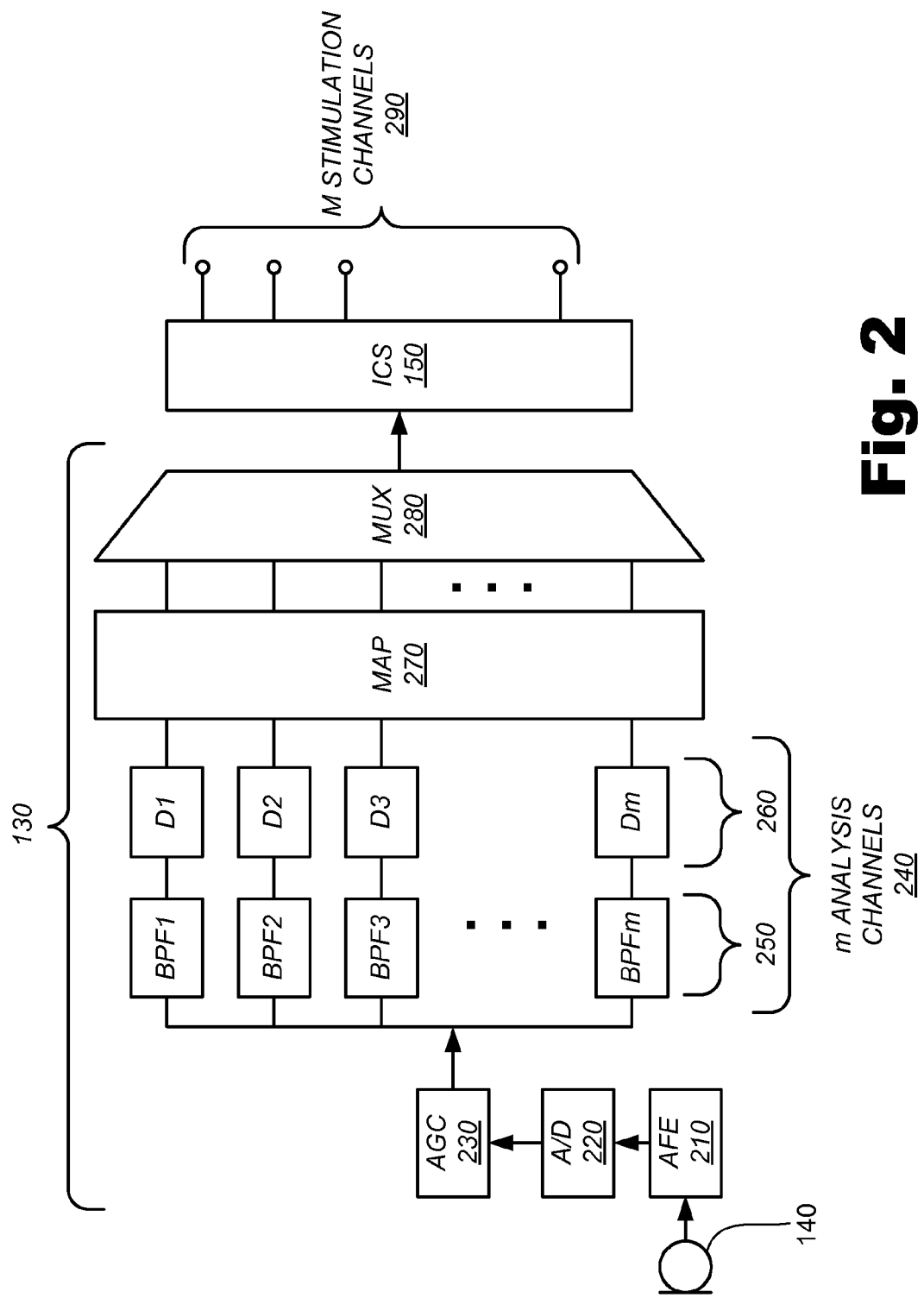
FIG. 2 is a functional block diagram of an exemplary sound processing unit and implantable cochlear stimulator according to principles described herein.

FIG. 2 is a functional block diagram of an exemplary sound processing unit 130 and implantable cochlear stimulator 150. The functions shown in FIG. 2 are merely representative of the many different functions that may be performed by the sound processing unit 130 and/or the implantable cochlear stimulator 150. A more complete description of the functional block diagram of the sound processing unit 130 and the implantable cochlear stimulator 150 is found in U.S. Pat. No. 6,219,580, which is incorporated herein by reference in its entirety.

As shown in FIG. 2, the microphone 140 senses acoustic information, such as speech and music, and converts the acoustic information into one or more electrical signals. These signals are then amplified in audio front-end (AFE) circuitry 210. The amplified audio signal is then converted to a digital signal by an analog-to-digital (A/D) converter 220. The resulting digital signal is then subjected to automatic gain control using a suitable automatic gain control (AGC) function 230.

After appropriate automatic gain control, the digital signal is then processed in one of a number of digital signal processing or analysis channels 240. For example, the sound processing unit 130 may include, but is not limited to, eight analysis channels 240. Each analysis channel 240 may respond to a different frequency content of the sensed acoustical signal. In other words, each analysis channel 240 includes a band-pass filter (BP1-BPFm) 250 or other type of filter such that the digital signal is divided into m analysis channels 240. The lowest frequency filter may be a low-pass filter, and the highest frequency filter may be a high-pass filter.

As shown in FIG. 2, each of the m analysis channels 240 may also include an energy detection stage (D1-Dm) 260. Each energy detection stage 260 may include any combination of circuitry configured to detect the amount of energy contained within each of the m analysis channels (240). For example, each energy detection stage 260 may include a rectification circuit followed by an integrator circuit. As will be described in more detail below, the cochlear implant system 100 may be configured to determine which of the m analysis channels 240 are presented to the patient via the stimulation channels 290 by analyzing the amount of energy contained in each of the m analysis channels 240.

After energy detection, the signals within each of the m analysis channels 240 are forwarded to a mapping stage 270. The mapping stage 270 is configured to map the signals in each of the m analysis channels 240 to one or more of M stimulation channels 290. In other words, the information contained in the m analysis channels 240 is used to define the stimulation pulses that are applied to the patient by the implantable cochlear stimulator 150 via the M stimulation channels 290. As mentioned previously, pairs or groups of individual electrodes 170 make up the M stimulation channels.

In some examples, the mapped signals are serialized by a multiplexer 128 and transmitted to the implantable cochlear stimulator 150. The implantable cochlear stimulator 150 may then apply stimulation current via one or more of the M stimulation channels 290 to one or more stimulation sites within the patient's cochlea. As used herein and in the appended claims, the term "stimulation site" will be used to refer to a target area or location at which the stimulation current is applied. For example, a stimulation site may refer to a particular location within the neural tissue of the cochlea. Through appropriate weighting and sharing of currents between the electrodes 170, stimulation current may be applied to any stimulation site along the length of the lead 180.

Figure 3:
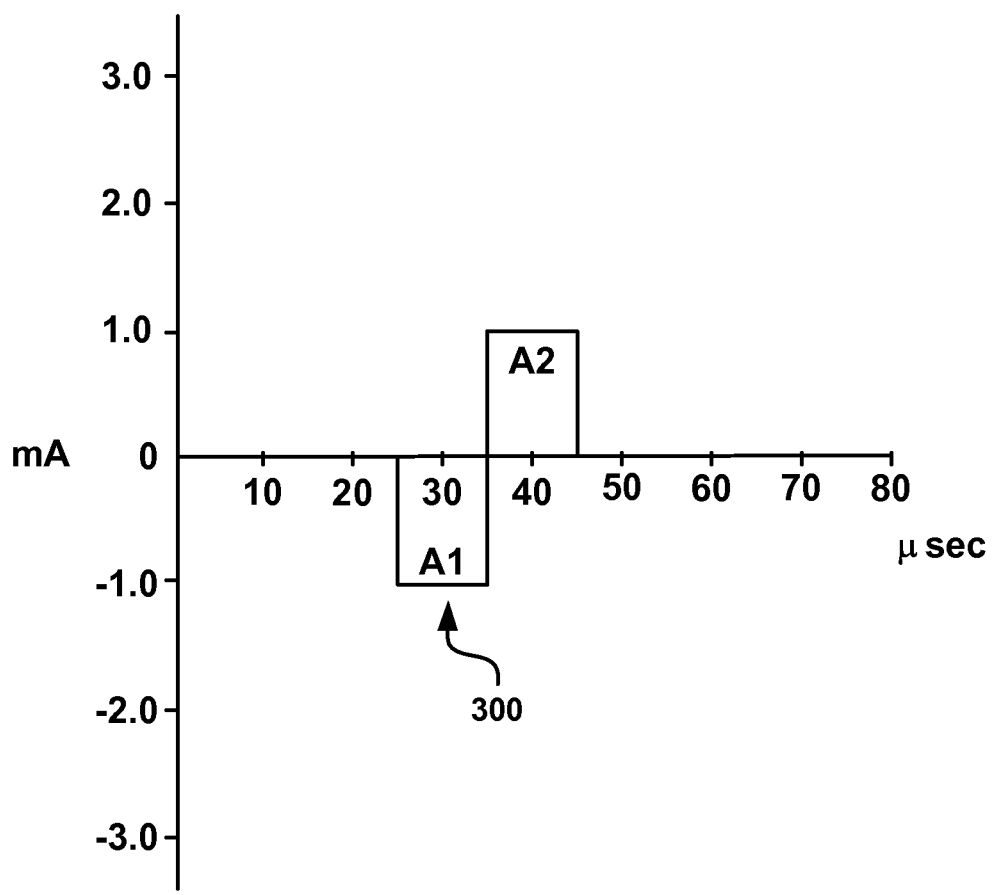
FIG. 3 illustrates an exemplary stimulation pulse according to principles described herein.

FIG. 3 illustrates an exemplary stimulation pulse 130 that may be delivered to neural tissue via one or more of the stimulation channels 290. The stimulation pulse 300 of FIG. 3 is biphasic. In other words, the pulse 300 includes two parts—a negative first phase having an area A1 and a positive second phase having an area A2. In some implementations, the negative phase A1 causes neural tissue to depolarize or fire. The biphasic stimulation pulse 300 shown in FIG. 3 has an amplitude of 1 milliamp (mA) and a pulse width of 20 microseconds ($\mu$ sec) for illustrative purposes only.

The combined areas of A1 and A2 are representative of a total amount of electric charge that is applied to a stimulation site by stimulation pulse 300. The biphasic stimulation pulse 300 shown in FIG. 3 is "charge-balanced" because the negative area A1 is equal to the positive area A2. A charge-balanced biphasic pulse is often employed as the stimulus to minimize electrode corrosion and charge build-up which can harm surrounding tissue. However, it will be recognized that the biphasic stimulation pulse 300 may alternatively be charge-imbalanced as best serves a particular application.

In some examples, the total amount of charge per phase applied to a stimulation site within the cochlea by a stimulation pulse 300 corresponds to a loudness level of an input audio signal as perceived by the patient. Hence, a change in the total amount of charge applied by a stimulation pulse 300 may result in a change in the loudness level of an audio signal, which may affect the sound quality of the audio signal as perceived by the patient.

Figure 4:
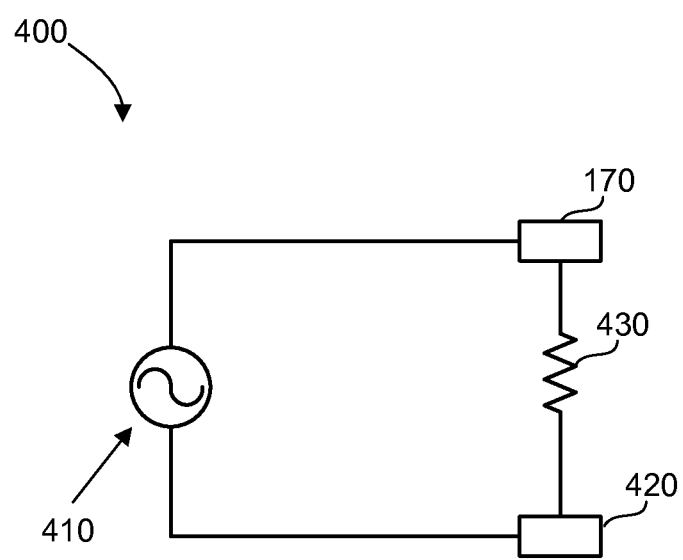
FIG. 4 illustrates an exemplary circuit diagram representative of a relationship between current applied to an electrode and the impedance of the electrode according to principles described herein.

One factor that may cause a change in the total charge per phase applied to a stimulation site is a change in electrode impedance. FIG. 4 will be used to illustrate the relationship between charge and electrode impedance.

FIG. 4 shows an exemplary circuit diagram 400 representative of a relationship between current applied to an electrode 170 and the impedance of the electrode 170. As shown in FIG. 4, the electrode 170 may be connected to a voltage source 410 configured to cause a current to be applied to the electrode 170. A return electrode 420 may also be included to complete the circuit. The return electrode 420 may include a ground, another one of the electrode 170, and/or the housing of the implantable cochlear stimulator 150. It will be assumed in the examples given herein that the return electrode 420 is ground.

As represented by resistor 430, an impedance may be associated with the electrode 170. The impedance may be dependent of the physiological properties of the tissue where the electrode 170 is implanted, the composition of the electrode 170 itself, and/or any other factor as may serve a particular application.

According to Ohm's law, the relationship between the voltage ("V") generated by voltage source 410, the current ("I") applied to the electrode 170, and the impedance ("Z") of the electrode 170 is V=I*Z. Thus, with a fixed maximum voltage, a change in impedance will cause an opposite change in the maximum current that may be applied to the electrode 170. For example, an increase in impedance would cause a decrease in maximum current, which in turn would cause a decrease in the total charge per phase applied to a stimulation site. This change in total charge applied to the stimulation site may have adverse effects on the loudness level or sound quality of an audio signal experienced by a patient. For example, a decrease in the total charge applied to the stimulation site may decrease the loudness level or sound quality of an audio signal experienced by a patient.

A change in electrode impedance may be caused by many different factors. For example, changes in one or more physiological properties of tissue within the cochlea, aging, a change in body fat percentage, introduction of scar tissue, dehydration, and/or infection may lead to a change in electrode impedance. A change in electrode impedance may additionally or alternatively be caused by an electrode malfunction (e.g., an electrode may become shorted or open). A change in electrode impedance may be permanent in some instances (e.g., with aging) or temporary in others (e.g., during an infection).

As mentioned, a change in electrode impedance may result in a degradation of sound quality experienced by a patient. For example, a change in electrode impedance may result in a change in loudness level and/or distort pitch.

Such sound quality degradation may adversely affect the ability of the patient to recognize speech, music, and/or other sounds. This can be especially devastating for pediatric cochlear implant patients because the change in sound quality or volume may go unnoticed for long periods of time. Hence, an undetected change in electrode impedance can potentially interfere with the overall speech and language development of pediatric patients. It will be recognized that cochlear implant patients of all ages may experience similar difficulties if a change in electrode impedance is not detected and accounted for. As will be discussed in more detail below, a change in impedance may be compensated for by adjusting one or more of the stimulation parameters. In some examples, the adjustment of stimulation parameters may be configured to maintain constant a total charge per phase applied to a stimulation site within the cochlea.

Figure 5:
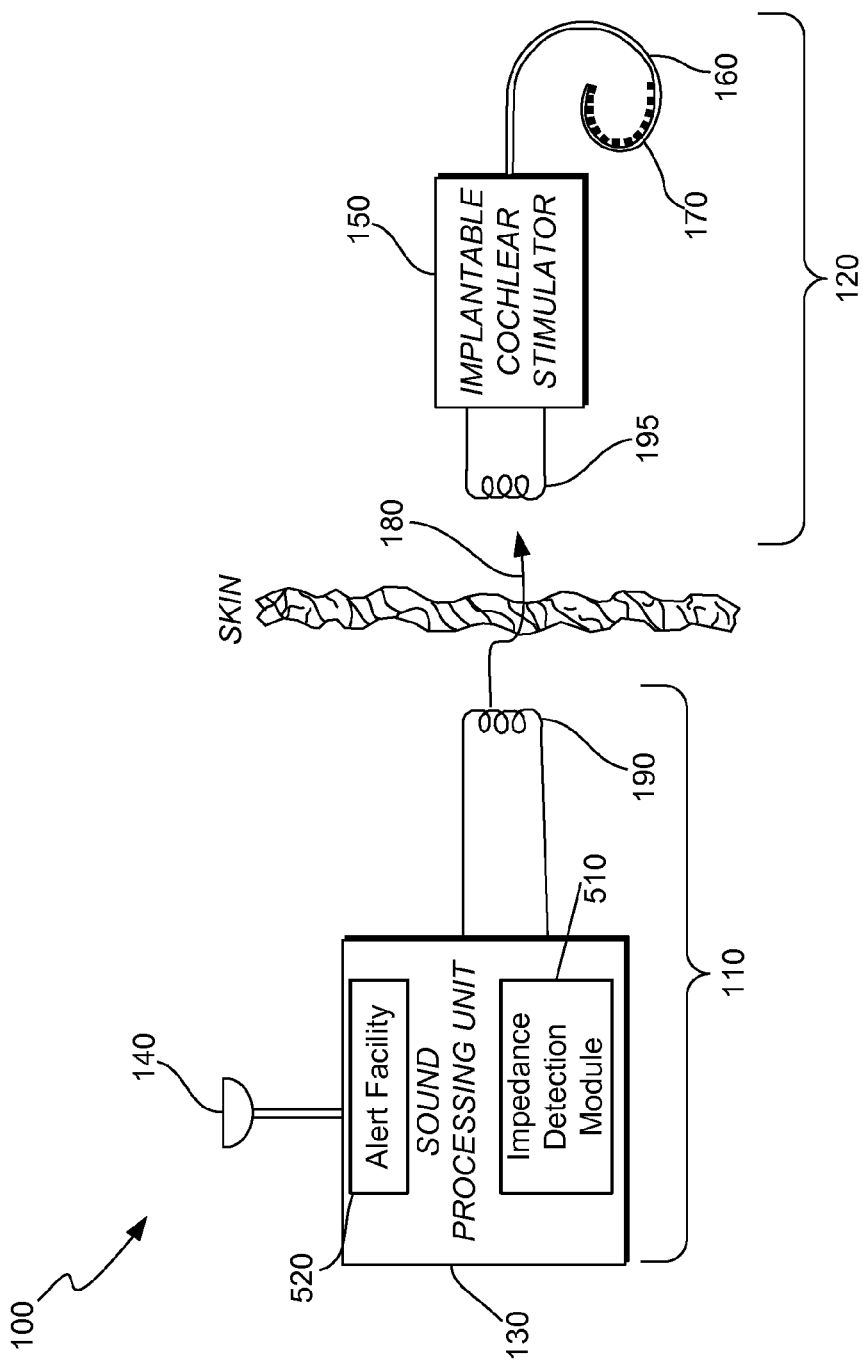
FIG. 5 depicts an exemplary implementation of the cochlear implant system of FIG. 1 according to principles described herein.

FIG. 5 depicts an exemplary implementation of cochlear implant system 100 that is configured to detect (e.g., automatically and/or in response to input provided by a user) an impedance of one or more electrodes 170 and perform one or more predefined actions accordingly in order to maintain an optimal perceived sound quality. As shown in FIG. 5, the sound processing unit 130 may include an impedance detection module 510 configured to detect an impedance of one or more of the electrodes 170. Impedance detection module 510 may include any combination of hardware, circuitry, and/or software configured to perform any of the functions described herein.

Impedance detection module 510 may be configured to detect one or more electrode impedances using any suitable technique. For example, the impedance detection module 510 may be configured to direct the implantable cochlear stimulator 150 to apply a pulse having a known amplitude to each of the electrodes 170 and then measure the resulting voltages at each electrode 170. The impedance may then be determined by the impedance detection module 510 by dividing the measured voltage by the known current. It will be recognized that any other method of detecting electrode impedances may be used as may serve a particular application.

In some examples, impedance detection module 510 may be configured to automatically detect one or more electrode impedances according to a predefined schedule. In one particular embodiment, the impedance detection module 510 may be configured to automatically measure the impedances of the electrodes 170 each time the implantable coil 195 and the external coil 190 are brought within range of one another after having been separated. For example, the sound processing unit 130 is often removed from its operating location (e.g., behind the ear) to be recharged or otherwise serviced. Additionally or alternatively, the sound processing unit 130 may be removed from its operating location when the patient goes to bed or at other times as the patient may desire. When the patient places the sound processing unit 130 back in its operating position, the impedance detection module 510 may automatically measure one or more electrode impedances.

Additionally or alternatively, the impedance detection module 510 may be configured to periodically measure one or more electrode impedances. For example, the impedance detection module 510 may measure one or more electrode impedances every twelve or twenty-four hours. It will be recognized that any time period may be used as may serve a particular application.

The predefined schedule may be such that the impedance detection module 510 is configured to measure one or more electrode impedances in response to a sensed condition. For example, the implantable cochlear stimulator 150 may be configured to transmit data to the sound processing unit 130 representative of a status of operation of the implantable cochlear stimulator 150. The sound processing unit 130 may analyze this data and determine that it is abnormal in some way. The impedance detection module 510 may be directed to measure one or more electrode impedances in response to the detected abnormality in order to determine whether a change in impedance has caused the abnormality. In some alternative examples, one or more electrode impedances may be measured whenever the user connects the sound processing unit 130 to the implanted electrodes 170.

In some examples, the sound processing unit 130 may be configured to maintain a log of electrode impedance measurements. In this manner, a change in one or more of the electrode impedances may be detected. The log may be stored as log data within one or more data storage units that are a part of or in communication with the sound processing unit 130.

The sound processing unit 130 may be configured to perform one or more predefined actions in accordance with the detected electrode impedances. For example, if the sound processing unit 130 determines that a change in electrode impedance has occurred, the predefined action may include alerting the patient or the patient's caregiver of the change in electrode impedance through the use of an audible or visual alert. In one implementation, this alert may only be provided if the change in impedance is deemed to cause an issue to quality of sound delivered to the patient. For example, an alert may be provided if it is ascertained that the implanted electronics are not able to deliver required stimulation because of compliance limitations inherent in the device. In this manner, the patient or the patient's caregiver may be put on notice that the patient may need to visit a clinician to readjust the stimulation parameters accordingly.

To this end, the sound processing unit 130 may include an alert facility 520 configured to convey one or more alerts to the patient and/or other user. The alert facility 520 may include any combination of hardware, circuitry, and/or software as may serve a particular application. For example, the alert facility 520 may include one or more LEDs or graphical interfaces configured to display a visual alert representative of a detected change in electrode impedance. Additionally or alternatively, the alert facility 520 may include circuitry configured to generate an audible beep or other sound representative of a detected change in electrode impedance. It will be recognized that other types of alerts (e.g., vibrating alerts, text messages, emails, etc.) may be generated by the alert facility 520 and communicated to the patient and/or other person as may serve a particular application.

Another predefined action that may be performed by the sound processing unit 130 in response to a detected change in electrode impedance includes adjusting one or more stimulation parameters to compensate for the detected change in electrode impedance. For example, if an increase in impedance for a particular electrode 170 is detected, the sound processing unit 130 may be configured to adjust one or more stimulation parameters such that the total electric charge applied via the electrode 170 remains constant. These changes may be made in order to attempt to maintain a consistent loudness level as perceived by the patient.

To illustrate, a stimulation pulse applied to a particular electrode 170 may be similar to that shown previously in FIG. 3. After processing the data acquired by the impedance detection module 510, the sound processing unit 130 may determine that the impedance of the electrode 170 has doubled. This change in impedance may result in the amplitude of the current applied to the electrode 170 being reduced by one half to a value of 0.5 mA.

Figure 6:
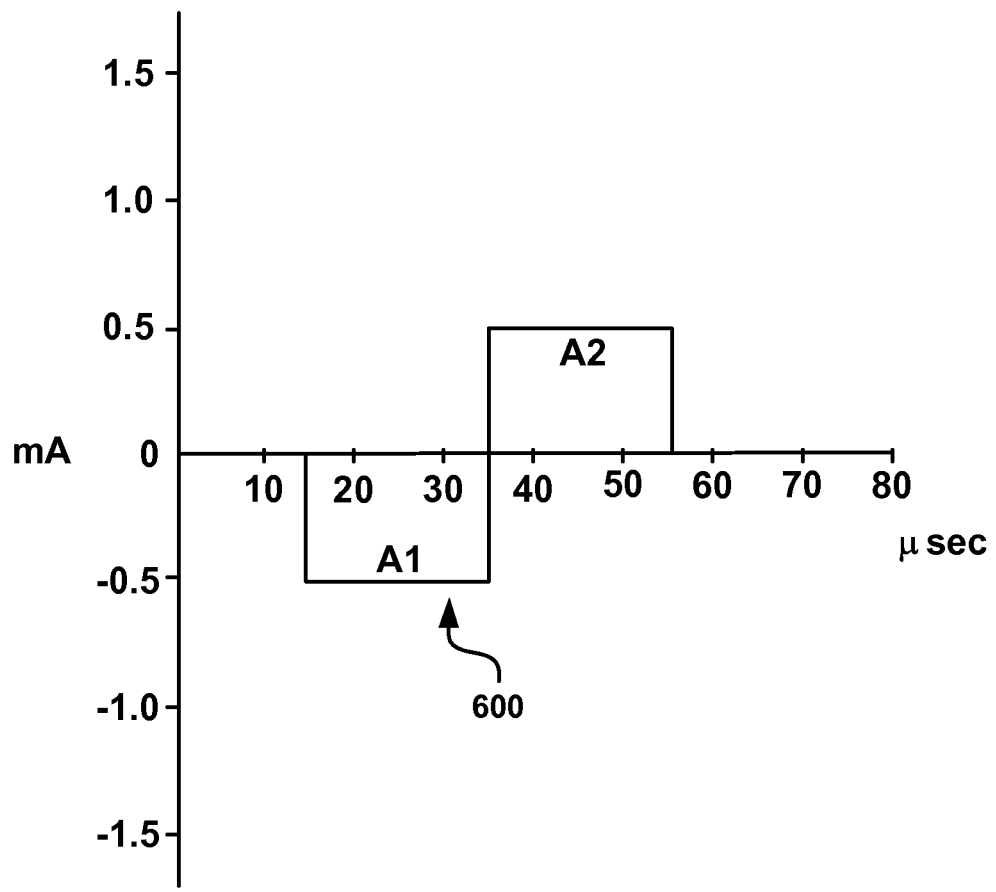
FIG. 6 illustrates an exemplary stimulation pulse according to principles described herein.

FIG. 6 illustrates an exemplary stimulation pulse 600 that may be delivered via the electrode 170 after the sound processing unit 130 has adjusted at least one stimulation parameter in response to the doubling in impedance of the electrode 170. As shown in FIG. 6, the pulse width of the stimulation pulse 600 has been doubled compared to the pulse width of stimulation pulse 300 shown in FIG. 3. In this manner, the total electric charge applied via the electrode 170 remains the same. It will be recognized that additional or alternative stimulation parameters governing the stimulation current applied via one or more electrodes 170 may be adjusted in response to a detected change in electrode impedance as may serve a particular application. Moreover, it will be recognized that the total charge per phase may be maintained constant using any other suitable method or technique.

Additional or alternative stimulation parameters may be adjusted to compensate for a detected change in electrode impedance. For example, a most comfortable stimulation level ("M level") and/or a quiet sound level ("T level") corresponding to electrical stimulation applied to a patient may be adjusted to compensate for a detected change in electrode impedance. Additionally or alternatively, values corresponding to a current amplitude versus pulse width curve may be stored in a look up table and used to determine an appropriate pulse width for a particular current amplitude caused by a change in impedance. These values may be obtained using any suitable heuristic and/or empirical data as may serve a particular application.

In some examples, sound processing unit 130 may adjust one or more stimulation parameters for only those electrodes i.e., channels) that have impedances that have changed (as opposed to adjusting one or more stimulation parameters for all of the electrodes in a multi-channel cochlear implant system).

For example, sound processing unit 130 may direct implantable cochlear stimulator 150 to apply a plurality of stimulation pulses each having a first pulse width by way of a plurality of electrodes during a first sequence of one or more stimulation frames. Sound processing unit 130 may subsequently detect a change in impedance of a particular electrode included in the plurality of electrodes. In response, sound processing unit 130 may adjust a pulse width parameter (and/or any other stimulation parameter) associated with the electrode to define a second pulse width that compensates for the change in impedance of the electrode. The pulse width parameter for the remaining electrodes included in the plurality of electrodes may remain unchanged. Consequently, during one or more stimulation frames subsequent to the first sequence of one or more stimulation frames, sound processing unit 130 may direct implantable cochlear stimulator 150 to apply one or more stimulation pulses having the second pulse width by way of the electrode and stimulation pulses having the first pulse width by way of the remaining electrodes.

Figure 7:
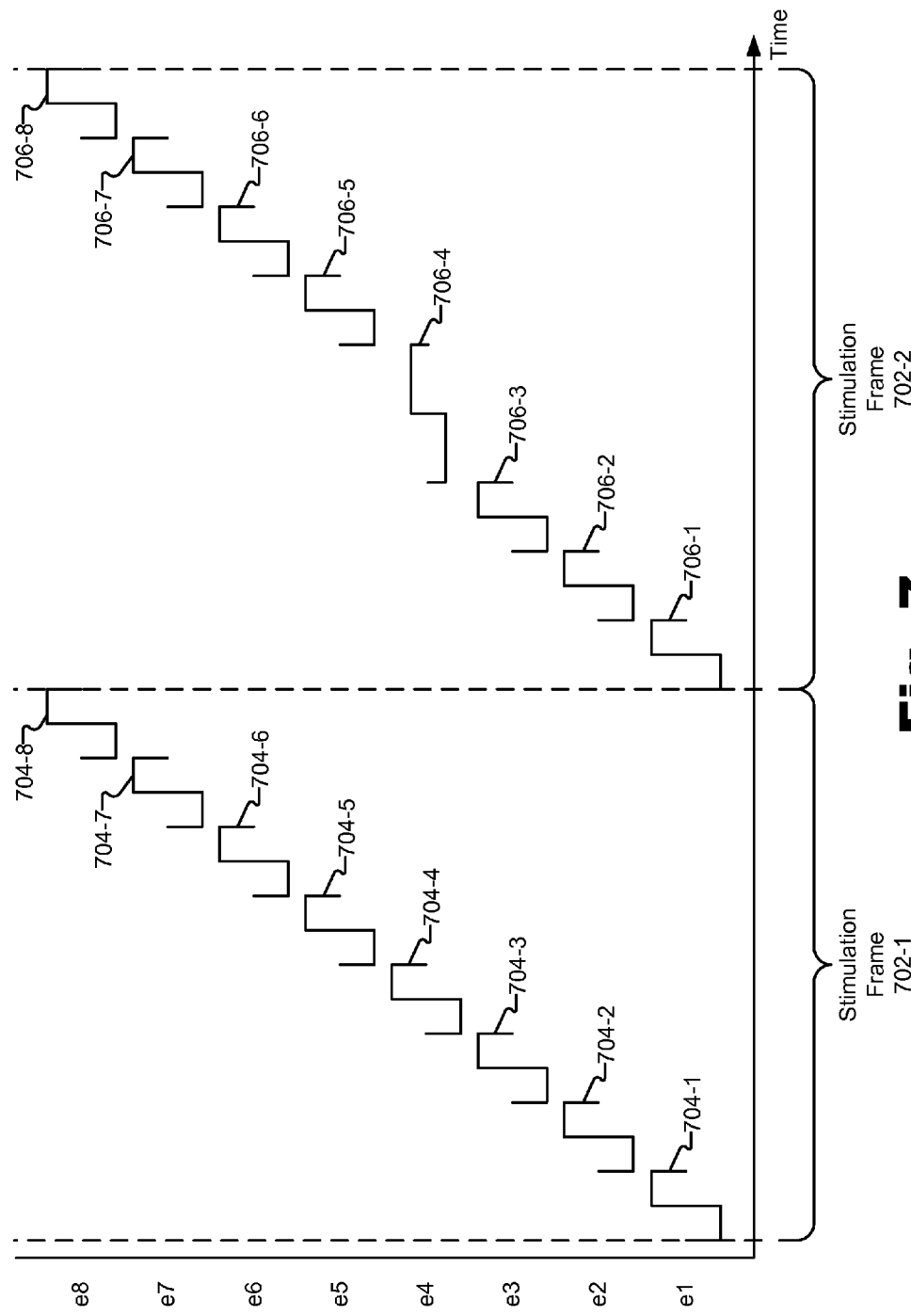
FIG. 7 shows an exemplary stimulation pulse sequence for a first stimulation frame and a second stimulation frame according to principles described herein.

To illustrate, FIG. 7 shows an exemplary stimulation pulse sequence for a first stimulation frame 702-1 and a second stimulation frame 702-2 (collectively "stimulation frames 702"). Second stimulation frame 702-2 may immediately follow first stimulation frame 702-1, as shown in FIG. 7. Alternatively, one or more other stimulation frames may temporally separate first and second stimulation frames 702 as may serve a particular implementation.

As shown, sound processing unit 130 may direct implantable cochlear stimulator 150 to apply a plurality of stimulation pulses 704 (e.g., stimulation pulses 704-1 through 704-8) by way of electrodes e1-e8 during first stimulation frame 702-1. Stimulation pulses 704 may be applied in any suitable manner. For example, stimulation pulses 704 may be sequentially applied by way of electrodes e1-e8 as shown in FIG. 7 (i.e., stimulation pulse 704-1 is applied by way of electrode e1, then stimulation pulse 704-2 is applied by way of electrode e2, and so on until stimulation pulse 704-8 is applied by way of electrode e8).

It will be recognized that the order in which stimulation pulses 704 are applied may vary as may serve a particular implementation. It will also be recognized that although FIG. 7 shows that only a single stimulation pulse 704 is applied at any given time, any number of stimulation pulses 704 may be applied concurrently. For example, stimulation pulses may be applied concurrently by way of adjacent electrodes (e.g., electrodes e1 and e2) that form a multi-electrode channel.

As shown, each stimulation pulse 704 has the same pulse width. This results in stimulation frame 702-1 having a duration of $8*PW_1$, where $PW_1$ is the pulse width associated with each stimulation pulse 704. Assuming the pulse width of each stimulation pulse 704 is 36 microseconds, stimulation frame 702-1 has a duration of 288 microseconds. Because there are eight stimulation pulses 704 in stimulation frame 702-1, the stimulation rate during stimulation frame 702-1 is equal to 8 pulses/288 microseconds, which is approximately equal to 27777.78 pulses per second.

In some examples, sound processing unit 130 may detect a change in impedance of electrode e4. For example, sound processing unit 130 may detect that the impedance of electrode e4 has increased. In response, sound processing unit 130 may adjust a pulse width parameter associated with electrode e4 to define a new pulse width that compensates for the change in impedance of electrode e4 (i.e., by maintaining a consistent loudness level and/or sound quality level of an audio signal as perceived by a patient associated with sound processing unit 130, as described above).

To illustrate, FIG. 7 shows a plurality of stimulation pulses 706 (e.g., stimulation pulses 706-1 through 706-8) that are applied by way of electrodes e1-e8 during a second stimulation frame 702-2 (i.e., during a stimulation frame that occurs subsequent to the pulse width parameter associated with electrode e4 being adjusted). As shown, the pulse width of the stimulation pulse 706-4 applied by way of electrode e4 has been increased and the amplitude of stimulation pulse 706-4 has been decreased in response to the change (i.e., increase) in impedance of electrode e4. However, the stimulation pulses applied by way of the remaining electrodes (i.e., stimulation pulses 706-1 through 706-3 and 706-5 through 706-8) still have the same pulse widths as the stimulation pulses 704 applied during the first stimulation frame 702-1.

By only increasing the pulse width associated with electrode e4 (as opposed to increasing the pulse width associated with each electrode), the stimulation rate is minimally affected. For example, the pulse width associated with electrode e4 may be increased to 72 microseconds compared to a pulse width of 36 microseconds that was associated with electrode e4 during stimulation frame 702-1. Assuming a pulse width of 36 microseconds is associated with the remaining electrodes during stimulation frame 702-2, stimulation frame 702-2 has a duration of 324 microseconds (i.e., $7*PW_1+PW_2$, where $PW_2$ is the new pulse width). Because there are eight stimulation pulses 706 in stimulation frame 702-2, the stimulation rate during stimulation frame 702-2 is equal to 8 pulses/324 microseconds, which is approximately equal to 24691.36 pulses per second. This is significantly higher than what the stimulation rate would be if the pulse width associated with all eight electrodes were increased to 72 microseconds (in that scenario, the stimulation rate would be half that of the stimulation rate associated with first stimulation frame 702-1 illustrated above).

It will be recognized that, in some examples, the impedances of multiple electrodes may change. In these examples, pulse width parameters associated with each of the multiple electrodes may be adjusted by sound processing unit 130 in a similar manner described above. It will also be recognized that although eight electrodes are illustrated in FIG. 7, any number of electrodes (e.g., sixteen) may be disposed on a lead configured to be implanted within a cochlear implant patient.

Figure 8:
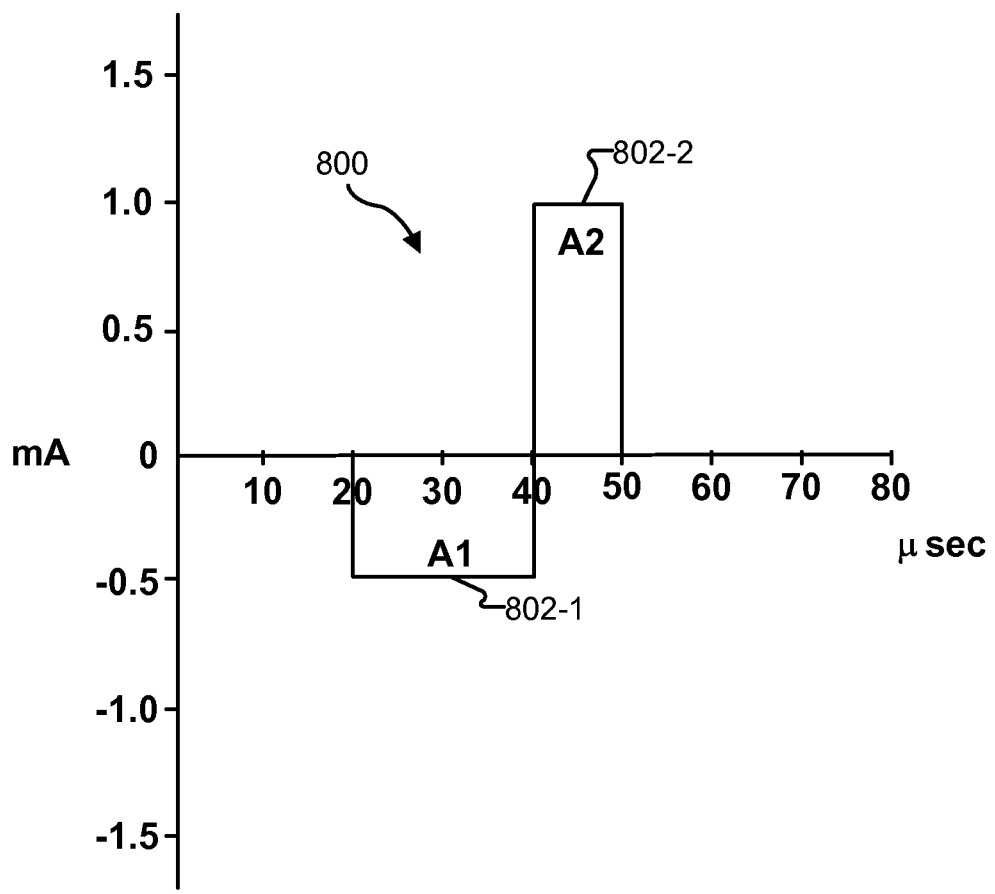
FIG. 8 illustrates an exemplary pseudomonphasic stimulation pulse according to principles described herein.

In some examples, sound processing unit 130 may adjust the pulse width parameter associated with an electrode that has a changed impedance in a manner that results in pseudomonphasic stimulation pulses being applied by way of the electrode. FIG. 8 illustrates an exemplary pseudomonphasic stimulation pulse 800 that may be applied by way of an electrode. As shown, pseudomonphasic stimulation pulse 800 may have a first phase 802-1 and a second phase 802-2 that differ in widths. For example, in the example of FIG. 8, first phase 802-1 has a width of approximately twenty microseconds and second phase 802-2 has a width of approximately ten microseconds. To keep pseudomonphasic stimulation pulse 800 charge-balanced, the amplitude of second phase 802-2 may be twice the amplitude of first phase 802-1, as shown in FIG. 8.

Other pulse shapes may also be used to compensate for a change in impedance of an electrode in accordance with the methods and systems described herein. For example, triphasic stimulation pulses (e.g., stimulation pulses that have a first negative phase followed by a positive phase followed by a second negative phase) may also be used to compensate for a change in impedance of an electrode.

Pseudomonphasic stimulation pulses, triphasic stimulation pulses, and other types of pulse shapes other than symmetric biphasic stimulation pulses may need lower current levels to achieve M levels as compared to symmetric biphasic stimulation pulses. Hence, the pulse width of these types of stimulation pulses may be minimally increased to compensate for a change in impedance of an electrode, thereby minimizing the impact on stimulation rate.

As mentioned, an electrode 170 that malfunctions or otherwise becomes disabled may result in a change in impedance of the electrode 170 and/or an abnormal impedance measurement. For example, an electrode 170 may become shorted or open. A shorted electrode 170 may have an impedance substantially equal to zero ohms. An open electrode 170 may have a relatively very large impedance value. Other electrode malfunctions may include, but are not limited to, partial shorting, irregular stimulation performance, etc. Such disabled electrodes may result in decreased sound quality and/or distorted pitch and may even render a cochlear implant system 100 useless to a patient.

In some examples, when the impedance detection module 510 detects an electrode impedance value indicative of a disabled electrode, the sound processing unit 130 may be configured to use current steering and/or other techniques to compensate for the disabled electrode. This is described more fully in the above-referenced U.S. patent application Ser. No. 13/571,679.

Figure 9:
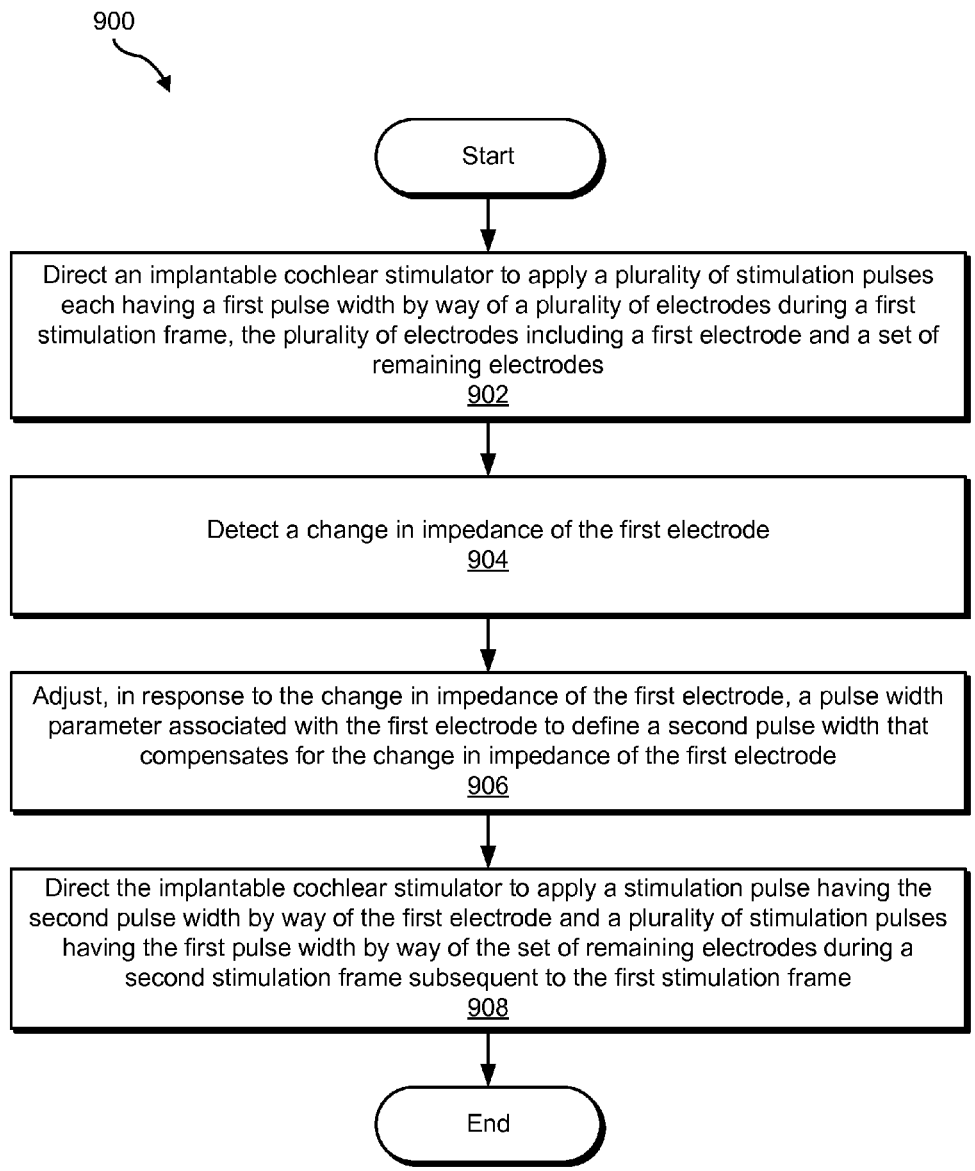
FIG. 9 illustrates an exemplary method of compensating for a change in impedance of an electrode according to principles described herein.

FIG. 9 illustrates an exemplary method 900 of compensating for a change in impedance of an electrode. While FIG. 9 illustrates exemplary steps according to one embodiment, other embodiments may omit, add to, reorder, and/or modify any of the steps shown in FIG. 9. One or more of the steps shown in FIG. 9 may be performed by sound processing unit 130 and/or any implementation thereof.

In step 902, a sound processing unit directs an implantable cochlear stimulator to apply a plurality of stimulation pulses each having a first pulse width by way of a plurality of electrodes during a first stimulation frame, the plurality of electrodes including a first electrode and a set of remaining electrodes. Step 902 may be performed in any of the ways described herein.

In step 904, the sound processing unit detects a change in impedance of the first electrode. Step 904 may be performed in any of the ways described herein.

In step 906, the sound processing unit adjusts, in response to the change in impedance of the first electrode, a pulse width parameter associated with the first electrode to define a second pulse width that compensates for the change in impedance of the first electrode. Step 906 may be performed in any of the ways described herein.

In step 908, the sound processing unit directs the implantable cochlear stimulator to apply a stimulation pulse having the second pulse width by way of the first electrode and a plurality of stimulation pulses having the first pulse width by way of the set of remaining electrodes during a second stimulation frame subsequent to the first stimulation frame. Step 908 may be performed in any of the ways described herein.

Figure 10:
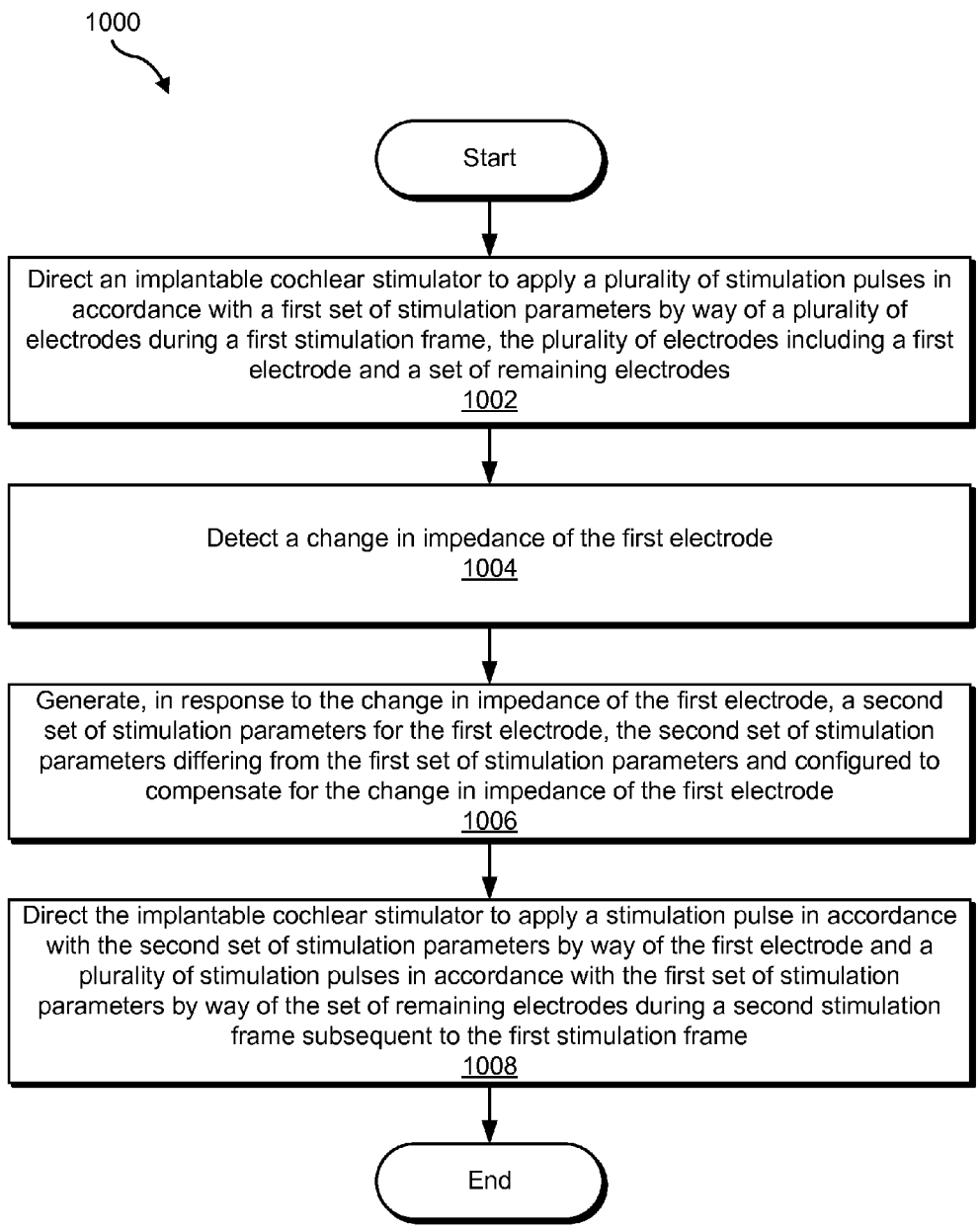
FIG. 10 illustrates another exemplary method of compensating for a change in impedance of an electrode according to principles described herein.

FIG. 10 illustrates another exemplary method 1000 of compensating for a change in impedance of an electrode. While FIG. 10 illustrates exemplary steps according to one embodiment, other embodiments may omit, add to, reorder, and/or modify any of the steps shown in FIG. 10. One or more of the steps shown in FIG. 10 may be performed by sound processing unit 130 and/or any implementation thereof.

In step 1002, a sound processing unit directs an implantable cochlear stimulator to apply a plurality of stimulation pulses in accordance with a first set of stimulation parameters by way of a plurality of electrodes during a first stimulation frame, the plurality of electrodes including a first electrode and a set of remaining electrodes. Step 1002 may be performed in any of the ways described herein.

In step 1004, the sound processing unit detects a change in impedance of the first electrode. Step 1004 may be performed in any of the ways described herein.

In step 1006, the sound processing unit generates, in response to the change in impedance of the first electrode, a second set of stimulation parameters for the first electrode, the second set of stimulation parameters differing from the first set of stimulation parameters and configured to compensate for the change in impedance of the first electrode. Step 1006 may be performed in any of the ways described herein. For example, the second set of stimulation parameters may include an adjusted pulse width parameter, an adjusted amplitude parameter, an adjusted pulse shape parameter, and/or any other adjusted stimulation parameter as may serve a particular implementation.

In step 1008, the sound processing unit directs the implantable cochlear stimulator to apply a stimulation pulse in accordance with the second set of stimulation parameters by way of the first electrode and a plurality of stimulation pulses in accordance with the first set of stimulation parameters by way of the set of remaining electrodes during a second stimulation frame subsequent to the first stimulation frame. Step 1008 may be performed in any of the ways described herein.

In the preceding description, various exemplary embodiments have been described with reference to the accompanying drawings. It will, however, be evident that various modifications and changes may be made thereto, and additional embodiments may be implemented, without departing from the scope of the invention as set forth in the claims that follow. For example, certain features of one embodiment described herein may be combined with or substituted for features of another embodiment described herein. The description and drawings are accordingly to be regarded in an illustrative rather than a restrictive sense.

What is claimed is:

1. A method comprising:
   directing, by a sound processing unit, an implantable cochlear stimulator to apply a plurality of stimulation pulses each having a first pulse width by way of a plurality of electrodes during a first stimulation frame, the plurality of electrodes including a first electrode and a set of remaining electrodes;

detecting, by the sound processing unit, a change in impedance of the first electrode;

adjusting, by the sound processing unit in response to the change in impedance of the first electrode, a pulse width parameter associated with the first electrode to define a second pulse width that compensates for the change in impedance of the first electrode; and directing, by the sound processing unit, the implantable cochlear stimulator to apply a stimulation pulse having the second pulse width by way of the first electrode and a plurality of stimulation pulses having the first pulse width by way of the set of remaining electrodes during a second stimulation frame subsequent to the first stimulation frame.

2. The method of claim 1, wherein the plurality of electrodes further includes a second electrode, and wherein the method further comprises:

detecting, by the sound processing unit, a change in impedance of the second electrode;

adjusting, in response to the change in impedance of the second electrode, a pulse width parameter associated with the second electrode to define a third pulse width that compensates for the change in impedance of the second electrode; and directing, by the sound processing unit, the implantable cochlear stimulator to apply a stimulation pulse having the third pulse width by way of the second electrode during the second stimulation frame.

3. The method of claim 1, wherein:

the change in impedance of the first electrode comprises an increase in impedance of the first electrode; and the adjusting comprises increasing the pulse width parameter so that the second pulse width is greater than the first pulse width.

4. The method of claim 3, wherein the stimulation pulse having the second pulse width is lower in amplitude than the stimulation pulses having the first pulse width.

5. The method of claim 1, wherein the stimulation pulse having the second pulse width is pseudomonphasic.

6. The method of claim 1, wherein the stimulation pulse having the second pulse width is at least triphasic.

7. The method of claim 1, wherein the plurality of electrodes includes a total of sixteen electrodes and the set of remaining electrodes includes fifteen electrodes.

8. The method of claim 1, wherein the detecting is performed in accordance with a predefined schedule.

9. The method of claim 8, wherein the predefined schedule comprises a periodic schedule.

10. The method of claim 1, wherein the detecting is performed each time the implantable cochlear stimulator is connected to the sound processing unit.

11. The method of claim 1, further comprising providing, by the sound processing unit, an alert indicative of the change in impedance.

12. The method of claim 1, wherein the second pulse width compensates for the change in impedance of the first electrode by maintaining a consistent loudness level of an audio signal as perceived by a patient associated with the sound processing unit.

13. The method of claim 1, wherein the second pulse width compensates for the change in impedance of the first electrode by maintaining a consistent sound quality of an audio signal as perceived by a patient associated with the sound processing unit.

14. A method comprising:

directing, by a sound processing unit, an implantable cochlear stimulator to apply a plurality of stimulation pulses in accordance with a first set of stimulation parameters by way of a plurality of electrodes during a first stimulation frame, the plurality of electrodes including a first electrode and a set of remaining electrodes;

detecting, by the sound processing unit, a change in impedance of the first electrode;

generating, by the sound processing unit in response to the change in impedance of the first electrode, a second set of stimulation parameters for the first electrode, the second set of stimulation parameters differing from the first set of stimulation parameters and configured to compensate for the change in impedance of the first electrode; and directing, by the sound processing unit, the implantable cochlear stimulator to apply a stimulation pulse in accordance with the second set of stimulation parameters by way of the first electrode and a plurality of stimulation pulses in accordance with the first set of stimulation parameters by way of the set of remaining electrodes during a second stimulation frame subsequent to the first stimulation frame.

15. The method of claim 14, wherein the generating of the second set of stimulation parameters comprises adjusting at least one stimulation parameter included in the first set of stimulation parameters.

16. The method of claim 15, wherein the adjusting of the at least one stimulation parameter included in the first set of stimulation parameters comprises adjusting at least one of a pulse width parameter and an amplitude parameter associated with the first electrode.

17. A system comprising:

a processor configured to direct an implantable cochlear stimulator to apply a plurality of stimulation pulses each having a first pulse width by way of a plurality of electrodes during a first stimulation frame, the plurality of electrodes including a first electrode and a set of remaining electrodes; and an impedance detection module communicatively coupled to the processor and configured to detect a change in impedance of the first electrode;

wherein the processor is further configured to adjust, in response to the change in impedance of the first electrode, a pulse width parameter associated with the first electrode to define a second pulse width that compensates for the change in impedance of the first electrode, and direct the implantable cochlear stimulator to apply a stimulation pulse having the second pulse width by way of the first electrode and a plurality of stimulation pulses having the first pulse width by way of the set of remaining electrodes during a second stimulation frame subsequent to the first stimulation frame.

18. The system of claim 17, wherein:

the change in impedance of the first electrode comprises an increase in impedance of the first electrode; and the processor is configured to adjust the pulse width parameter by increasing the pulse width parameter so that the second pulse width is wider than the first pulse width.

19. The system of claim 18, wherein the stimulation pulse having the second pulse width is lower in amplitude than the stimulation pulses having the first pulse width.

20. The system of claim 17, wherein the stimulation pulse having the second pulse width is pseudomonphasic.

* * * * *